United States Patent
Arlt et al.

[11] Patent Number: 5,869,516
[45] Date of Patent: *Feb. 9, 1999

[54] 4-(ARYLAMINOMETHYLENE)-2,4-DIHYDRO-3-PYRAZOLONES

[75] Inventors: Michael Arlt, Seeheim; Rochus Jonas, Darmstadt; Maria Christadler, Rodermark; Gunter Schneider, Gross Bieberau; Michael Klockow, Rossdorf, all of Germany

[73] Assignee: Merck Patent Gesellschaft mit beschrankter Haftung, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 648,951

[22] Filed: May 16, 1996

[30] Foreign Application Priority Data

May 17, 1995 [DE] Germany .................. 195 18 082.8

[51] Int. Cl.⁶ .................. A61K 31/415; C07D 231/22
[52] U.S. Cl. .................. 514/404; 548/364.1; 548/370.1
[58] Field of Search .................. 548/370.1, 364.1; 514/404

[56] References Cited

U.S. PATENT DOCUMENTS

| | | | |
|---|---|---|---|
| 4,355,159 | 10/1982 | Iqbal et al. . | |
| 4,460,768 | 7/1984 | Iqbal et al. . | |
| 4,880,804 | 11/1989 | Carini et al. | 514/234.5 |
| 4,909,827 | 3/1990 | Gehring et al. | 514/404 |
| 5,028,717 | 7/1991 | Gehring et al. . | |
| 5,162,528 | 11/1992 | Gehring et al. | 544/140 |

FOREIGN PATENT DOCUMENTS

| | | |
|---|---|---|
| 020-299 | 12/1980 | European Pat. Off. . |
| 201 188 | 4/1986 | European Pat. Off. . |
| 274 642 | 12/1987 | European Pat. Off. . |
| 93/06104 | 4/1993 | WIPO . |

OTHER PUBLICATIONS

Wolfbeis, Ein effiziente Synthese . . . , Monatshefte für Chemie, Bd. 112, pp. 369–383, 1981.
Nardi et al., "Pyrazolin–5–one and . . . ", Arzneimittel–Forschung, Bd. 19, No, 10, pp. 1721–1723, 1969.
Freyer et al., "Syntheses von tautomeriefahigen . . . ", J. f. Prakat Chemie, Band 319, Heft 6, 1977, pp. 905–910.
Kruetzberger et al., "Entzungshemmende Wirkstoffe, 10.Mitt.", Archiv der Pharmazie, Band 319, Heft 10, pp. 865–871, Oct. 1986.
Rockley, JE and Summers, LA, Structure of 5–Methyl–4 [(arylamino)methylene]–2,4–dihydro–3H–pyrazol–3–ones. Aust. J. Chem., 34: 1117–24, 1981.
Keats et al., Mass Spectral Fragmentation Pattern of 5–Methyl–4–[(phenylamino)methylene]–2,4–dihydro–3H–pyrazol–3–one and its 2–Methyl and 2–Phenyl Derivatives. J. Heterocyclic Chem., 19: 55–59, 1982.
Wolfbeis, "Eine effiziete Synthese von Aminoalkylidenederivaten . . . ". Monatshefte fur Chemie, vol. 112, pp. 369–383, 1981.

Primary Examiner—Jose G. Dees
Assistant Examiner—Barbara Badio
Attorney, Agent, or Firm—Miller, White, Zelano, & Branigan, P.C.

[57] ABSTRACT

5-Pyrazolinone derivatives of the general formula I:

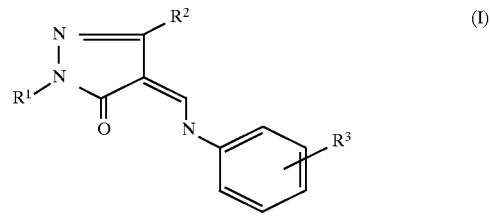

in which the $R^1$–$R^3$ variables are as defined herein and the physiologically acceptable salts thereof; processes for the preparation of these compounds, and in particular their use as selective inhibitors of cGMP-specific phosphodiesterase (cGMP PDE), thus as pharmaceutically active compounds.

13 Claims, No Drawings

4-(ARYLAMINOMETHYLENE)-2,4-DIHYDRO-3-PYRAZOLONES

The invention relates to 5-pyrazolinone derivatives of the general formula I:

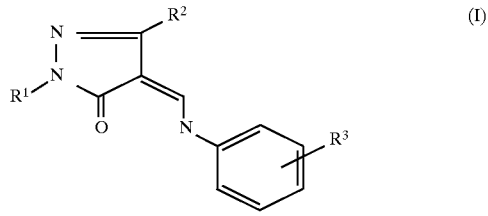

in which
- $R^1$ is benzyl; alkoxybenzyl with 1–3 C atoms in the alkoxy moiety; phenyl; phenyl which is substituted once to three times by amino, halogen, $NO_2$, CN, acyl, AO—, $HSO_3$—, $CO_2H$, A—O—CO—, A—CO—NH—, A—CO—NA—, carbamoyl, N-alkylcarbamoyl, N,N-dialkylcarbamoyl (with 1–6 C atoms in each alkyl moiety), A—O—CO—NH—, A—O—CO—NA—, $SO_2NR^4R^5$($R^4$ and $R^5$ can be independently H or alkyl with 1–6 C atoms, or $NR^4R^5$ is a 5- or 6-membered ring, optionally with other heteroatoms such as N, S, O, which ring may be substituted by A), A—CO—NH—$SO_2$—, A—CO—NA—$SO_2$—, A—$SO_2$—NH—, A—$SO_2$—NA—, (A—$SO_2$—)$_2$N—, A—CO—$SO_2$—NA—, A—CO—$SO_2$—NH—, tetrazolyl or phospho ($PO_3H_2$); or pyridyl;
- $R^2$ is alkyl, alkoxycarbonylalkyl, hydroxyalkyl, or hydroxycarbonylalkyl, where the alkyl and alkoxy groups independently preferably have 1–6 C atoms, more preferably 1–5 C atoms;
- $R^3$ is H, straight-chain or branched alkyl, straight-chain or branched alkoxy, fluorine- or chlorine-substituted alkyl, aminoalkanoyl, aminoalkyl, carbamoyl, $SO_2NR^4R^5$ ($R^4$ and $R^5$, independently, can be H or alkyl, or $NR^4R^5$ is a 5- or 6-membered ring, optionally with other heteroatoms such as N, S, O, which ring may be substituted by A), where the alkyl and alkoxy groups independently preferably have 1–6 C atoms, more preferably 1–5 C atoms;
- A is straight or branched alkyl with 1–6 C atoms or straight or branched flourine- or chlorine substituted alkyl with 1–6 C atoms, and the physiologically acceptable salts thereof.

Part of the invention also comprises processes for the preparation of these compounds, but in particular their use as selective inhibitors of cGMP-specific phosphodiesterase (cGMP PDE) and thus as pharmaceutically active compounds.

These compounds may, in some cases, have other utilities. The invention is particularly concerned with their activity as cGMP PDE inhibitors and their use therapeutically in various medical sections. They can be used in particular for the treatment of disorders of the cardiovascular system, of heart failure, of arteriosclerosis and other symptoms caused by disturbances of the function of the coronary vessels of the heart.

BACKGROUND OF THE INVENTION

A large number of compounds which have an inhibitory effect on cGMP PD esterases are disclosed in the literature.

Thus, EP-A1 0201 188 describes pyrazolo[4,3-d]-pyrimidin-7-ones as adenosine receptor antagonists and PDE inhibitors which can be used for the treatment of disorders of the coronary vessels of the heart associated with heart failure or cardiac insufficiency. However, this publication gives no examples of these compounds, nor are they particularly effective PDE inhibitors, in particular for cGMP PDE.

WO-A1 93/06104 describes substitutedpyrazolo[4,3-d] pyrimidin-7-ones with an inhibitory specificity for cGMP PD esterases by comparison with that for cAMP PD esterases which is improved by comparison with the class of compounds disclosed in the aforementioned publication. The selectivity of these compounds for the other phosphodiesterases I, II and III is, however, not mentioned in this publication.

However, the simultaneous inhibitory effect of a compound on the other phosphodiesterases is of great importance to their utility because when there is a simultaneous inhibitory effect on other esterases apart from cGMP phosphodiesterase (PDE V) a whole range of unwanted side effects may emerge when it is used as medicament.

SUMMARY OF THE INVENTION

It is therefore an object of this invention to provide compounds which have a particularly pronounced inhibitory effect on cGMP phosphodiesterases (PDE V) but at the same time show no, or such a low, inhibition on the other phosphodiesterases that there are no detectable side effects attributable to inhibition of PD esterases I–IV.

At the same time, it is an object of this invention to provide a process by which the corresponding compounds can be prepared in yields which are as high as possible and in purities which are as high as possible.

Upon further study of the specification and appended claims, further objects and advantages of this invention will become apparent to those skilled in the art.

It has now been found that compounds of the formula (I)

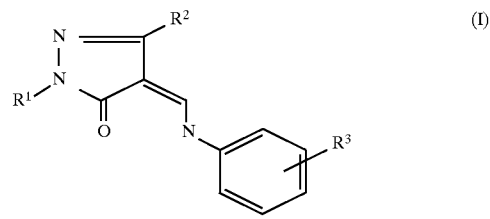

in which
- $R^1$ is benzyl; alkoxybenzyl with 1–3 C atoms in the alkoxy moiety; phenyl; phenyl which is substituted once to three times by amino, halogen, $NO_2$, CN, acyl, AO—, $HSO_3$—, $CO_2H$, A—O—CO—, A—CO—NH—, A—CO—NA—, carbamoyl, N-alkylcarbamoyl, N,N-dialkylcarbamoyl (with 1–6 C atoms in each alkyl moiety), A—O—CO—NH—, A—O—CO—NA—, $SO_2NR^4R^5$($R^4$ and $R^5$ can be H or alkyl with 1–6 C atoms, or $NR^4R^5$ is a 5- or 6-membered ring, optionally with other heteroatoms such as N, S, O, which ring may be substituted by A), A—CO—NH—$SO_2$—, A—CO—NA—$SO_2$—, A—$SO_2$—NH—, A—$SO_2$—NA—, (A—$SO_2$—)$_2$N—, tetrazolyl or phospho; or pyridyl;
- $R^2$ is alkyl with 1–5 C atoms, alkoxycarbonylalkyl, hydroxyalkyl, hydroxycarbonylalkyl;
- $R^3$ is H, straight-chain or branched alkyl with 1–5 C atoms, straight-chain or branched alkoxy with 1–5 C atoms, fluorine- or chlorine-substituted alkyl, aminoalkanoyl, aminoalkyl, carbamoyl, $SO_2NR^4R^5$ ($R^4$ and $R^5$ can be H or alkyl with 1–6 C atoms, or $NR^4R^5$ is a 5- or 6-membered ring, optionally with other heteroatoms such as N, S, O, which ring may be substituted by A);

A is straight or branched alkyl with 1–6 C atoms or straight or branched flourine- or chlorine substituted alkyl with 1–6 C atoms, or their salts, achieve this object.

The invention furthermore relates to the novel compounds of the general formula (I) in which $R^1$ is phenyl or phenyl which is substituted once to three times by halogen, nitro, cyano, carboxyl or amino, and $R^2$ is hydroxyalkyl and $R^3$ is H, straight-chain or branched alkyl with 1–5 C atoms, straight-chain or branched alkoxy with 1–5 C atoms, fluorine- or chlorine-substituted alkyl, or their salts.

Preferred compounds of the general formula (I) are those in which $R^1$ is as recited in the broadest sense for general formula (I), and $R^2$ is $H_5C_2$—O—CO—$CH_2$— and $R^3$ is aminoalkanoyl, alkanoylamino, carbamoyl, $SO_2NR^4R^5$ ($R^4$ and $R^5$ can be H or alkyl with 1–6 C atoms, or $NR^4R^5$ is a 5- or 6-membered ring, optionally with other heteroatoms such as N, S, O, which ring may be substituted by A), or their salts.

The invention particularly relates to the compounds

Methyl N-(3-(4-(2-ethylanilinomethylene)-4,5-dihydro-3-methyl-5-oxo-1H-pyrazol-1-yl)phenyl)carbamate 4-((2-Ethoxyanilinomethylene)-4,5-dihydro-3 -methyl-5-oxo-1H-pyrazol-1-yl)-N-ethylbenzenesulfonamide Ethyl 2-(1-(4-(N,N-diethylsulfamoyl)phenyl)-4-(2-ethylanilinomethylene)-4,5-dihydro-5-oxo-1H-pyrazol-3-yl)acetate Ethyl 2-(1-(4-(N,N-diethylsulfamoyl)phenyl)-4-(2-ethylanilinomethylene)-4,5-dihydro-5-oxo-1H-pyrazol-3-yl)acetate Ethyl 2-(1-(4-acetamidophenyl)-4-(2-ethylanilinomethylene)-4,5-dihydro-5-oxo-1H-pyrazol-3-yl)acetate Ethyl 2-(4-(2-ethylanilinomethylene)-4,5-dihydro-5-oxo-1-(4-trifluoroacetamidophenyl)-1H-pyrazol-3-yl)acetate Ethyl 2-(1-(4-ethoxycarbonylaminophenyl)-4-(2-ethylanilinomethylene)-4,5-dihydro-5-oxo-1H-pyrazol-3-yl)acetate Ethyl 2-(4-(2-ethylanilinomethylene)-4,5-dihydro-1-(4-methanesulfonamidophenyl)-5-oxo-1H-pyrazol-3-yl)acetate N-(3-(4-(2-Ethylanilinomethylene)-4,5-dihydro-3-methyl-5-oxo-5H-pyrazol-1-yl)phenyl)acetamide N,N-Diethyl-4-(4-(2-ethylanilinomethylene)-4,5-dihydro-3-methyl-5-oxo-1H-pyrazol-1-yl)benzenesulfonamide N-Ethyl-4-(4-(2-ethylanilinomethylene)-4,5-dihydro-3-methyl-5-oxo-1H-pyrazol-1-yl)benzenesulfonamide 4-(2-Ethoxyanilinomethylene)-2,4-dihydro-5-methyl-2-(4-(4-morpholinylsulfonyl)phenyl)-3H-pyrazol-3-one 4-(2-Ethylanilinomethylene)-2,4-dihydro-5-methyl-2-(4-(4-methyl-1-piperazinylsulfonyl)phenyl)-3H-pyrazol-3-one N-(3-(4-(2-Ethylanilinomethylene)-4,5-dihydro-3 -methyl-5-oxo-1H-pyrazol-1-yl)phenyl)methanesulfonamide N-(3-(4-(2-Ethylanilinomethylene)-4,5-dihydro-3-methyl-5-oxo-1H-pyrazol-5-yl)phenyl)trifluoroacetamide N-(4-(4-(2-Ethylanilinomethylene)-4,5-dihydro-3-methyl-5-oxo-1H-pyrazol-1-yl)phenyl)-N-methylsulfonylmethanesulfonamide N,N-Diethyl-4-(4,5-dihydro-4-(2-ethoxyanilinomethylene)-3-methyl-5-oxo-1H-pyrazol-1-yl)benzenesulfonamide N,N-Diethyl-4-(4,5-dihydro-4-(2-methoxyanilinomethylene)-3-methyl-5-oxo-1H-pyrazol-1-yl)benzenesulfonamide 3-(4-(2-Ethylanilinomethylene)-4,5-dihydro-5-oxo-3-propyl-1H-pyrazol-1-yl)benzenesulfonic acid 4-(4-(2-Ethylanilinomethylene)-4,5-dihydro-5-oxo-3-propyl-1H-pyrazol-1-yl)benzenesulfonic acid Ethyl 2-(4-(2-ethylanilinomethylene)-4,5-dihydro-1-(4-nitrophenyl)-5-oxo-1H-pyrazol-3-yl)acetate 4-(4-(2-Ethylanilinomethylene)-4,5-dihydro-5-oxo-3-propyl-1H-pyrazol-1-yl)benzoic acid 4-(4-(2-Ethylanilinomethylene)-4,5-dihydro-3-methyl-5-oxo-1H-pyrazol-1-yl)-N-hexylbenzamide 4-(4-(2-Ethylanilinomethylene)-4,5-dihydro-3-methyl-5-oxo-1H-pyrazol-1-yl)benzamide N,N-Diethyl-4-(4-(2-ethylanilinomethylene)-4,5-dihydro-3-methyl-5-oxo-1H-pyrazol-1-yl)benzamide 4-(2-Ethylanilinomethylene)-2,4-dihydro-5-propyl-2-(4-pyridyl)-3H-pyrazol-3-one N,N-Diethyl-4-(4-(2-ethylanilinomethylene)-4,5-dihydro-5-oxo-3-propyl-1H-pyrazol-1-yl)benzamide 4-(4-(2-Ethylanilinomethylene)-4,5-dihydro-5-oxo-3-propyl-1H-pyrazol-1-yl)-N-hexylbenzamide 4-(4-(2-Ethylanilinomethylene)-4,5-dihydro-5-oxo-3-propyl-1H-pyrazol-1-yl)benzamide 4-(4-(2-Ethylanilinomethylene)-4,5-dihydro-5-oxo-3-propyl-1H-pyrazol-1-yl)benzoic acid 4-(2-Ethylanilinomethylene)-2,4-dihydro-5-propyl-2-(4-(1H-tetrazol-5-yl)phenyl)-3H-pyrazol-3-one 4-(2-Ethylanilinomethylene)-2,4-dihydro-5-methyl-2-(3-(1H-tetrazol-5-yl)phenyl)-3H-pyrazol-3-one 4-(4,5-Dihydro-3-methyl-5-oxo-4-(2-trifluoromethylanilinomethylene)-1H-pyrazol-1-yl)benzoic acid 4-(4-(2-Ethylanilinomethylene)-3-ethoxycarbonylmethyl4,5-dihydro-5-oxo-1H-pyrazol-1-yl)benzoic acid 4-(4,5-Dihydro-3-methyl-5-oxo-4-(2-(2-propynyloxy)-anilinomethylene)-1H-pyrazol-1-yl)benzoic acid 4-(4,5-Dihydro-3-methyl-5-oxo-4-(2-propoxyanilinomethylene)-1H-pyrazol-1-yl)benzoic acid 4-(4,5-Dihydro-4-(2-isopropylanilinomethylene)-3-methyl-5-oxo-1H-pyrazol-1-yl)benzoic acid 3-(4-(2-Ethylanilinomethyleneaminomethylene)-4,5-dihydro-3-methyl-5-oxo-1H-pyrazol-1-yl)benzenesulfonamide Ethyl 2-(1-(4-acetamidophenyl)4-(2-ethylanilinomethylene)4,5-dihydro-5-oxo-1H-pyrazol-3-yl)acetate Ethyl 2-(4-(2-ethylanilinomethylene)-4,5-dihydro-1-(4-trifluoroacetamidophenyl)-5-oxo-1H-pyrazol-3-yl)acetate Ethyl 2-(1-(4-methoxycarbonylaminophenyl)-4-(2-ethylanilinomethylene)-4,5-dihydro-5-oxo-1H-pyrazol-3-yl)acetate Ethyl 2-(4-(2-ethylanilinomethylene)-4,5-dihydro-1-(4-methanesulfonamidophenyl)-5-oxo-1H-pyrazol-3-yl)acetate Ethyl 2-(1-(4-(N,N-diethylsulfamoyl)-phenyl)-4-(2-ethylanilinomethylene)-4,5-dihydro-5-oxo-1H-pyrazol-3-yl)-acetate Ethyl 2-(1-(4-(N,N-diethylsulfamoyl)-phenyl)-4-(2-ethoxyanilinomethylene)-4,5-dihydro-5-oxo-1H-pyrazol-3-yl)-acetate Ethyl 2-(1-(4-acetamidophenyl)-4-(2-ethylanilinomethylene)-4,5-dihydro-5-oxo-1H-pyrazol-3-yl)-acetate Ethyl 2-(4-(2-ethylanilinomethylene)-4,5-dihydro-5-oxo-1-(4-trifluoroacetamidophenyl)1H-pyrazol-3-yl)-acetate Ethyl 2-(4-(2-ethylanilinomethylene)-4,5-dihydro-1-(4-methoxycarbonylaminophenyl)-5-oxo-1H-pyrazol-3-yl)-acetate Ethyl 2-(4-(2-ethylanilinomethylene)-4,5-dihydro-1-(4-methanesulfonamidophenyl)-5-oxo-1H-pyrazol-3-yl)-acetate Ethyl 2-(1-(4-acetamidophenyl)-4-(2-ethylanilinomethylene)-4,5-dihydro-5-oxo-1H-pyrazol-3-yl)-acetate 2-(4-(2-Ethylanilinomethylene)-4,5-dihydro-1-(4-methoxycarbonylaminophenyl)-5-oxo-1H-pyrazol-3-yl)-acetic acid N-(3-(4-(2-Ethylanilinomethylene)-4,5-dihydro-5-oxo-3-propyl-1H-pyrazol-1-yl)-phenyl)-methanesulfonamide N-(3-(4-(2-Ethylanilinomethylene)-4,5-dihydro-5-oxo-3-propyl-1H-pyrazol-1-yl)-phenyl)acetamide Methyl N-(3-(4-(2-ethylanilinomethylene)-4,5-dihydro-5-oxo-3-propyl-1H-pyrazol-1-yl)-phenyl)-carbamate Ethyl 2-(4-(2-ethylanilinomethylene)-4,5-dihydro-5-oxo-1-(3-trifluoroacetamidophenyl)-1H-pyrazol-1-yl)-acetate Ethyl 2-(4-(2-ethylanilinomethylene)-4,5-dihydro-1-(3-methanesulfonamidophenyl)-5-oxo-1H-pyrazol-3-yl)-acetate and their physiologically acceptable salts.

The invention particularly relates to medicaments of the general formula (I) in which $R^1$ is benzyl; alkoxybenzyl with 1–3 C atoms in the alkoxy moiety; phenyl; phenyl which is substituted once to three times by amino, halogen, $NO_2$, CN, acyl, AO—, $HSO_3$—, $CO_2H$, A—O—CO—, A—CO—NH—, A—CO—NA—, carbamoyl, N-alkylcarbamoyl, N,N-dialkylcarbamoyl (with 1–6 C atoms in each alkyl moiety), A—O—CO—NH—, A—O—CO—NA—, $SO_2NR^4R^5$ ($R^4$ and $R^5$ can be H or alkyl with 1–6 C atoms, or $NR^4R^5$ is a 5- or 6-membered ring, optionally with other heteroatoms such as N, S, O, which ring may be substituted by A), A—CO—NH—$SO_2$—, A—CO—NA—$SO_2$—, A—$SO_2$—NH—, A—$SO_2$—NA—, (A—$SO_2$—)$_2$N—, tetrazolyl or phospho; or pyridyl;

$R^2$ is alkyl with 1–5 C atoms, alkoxycarbonylalkyl, hydroxyalkyl, hydroxycarbonylalkyl;

$R^3$ is H, straight-chain or branched alkyl with 1–5 C atoms, straight-chain or branched alkoxy with 1–5 C atoms, fluorine- or chlorine-substituted alkyl, aminoalkanoyl, aminoalkyl, $SO_2NR^4R^5$ ($R^4$ and $R^5$ can be H or alkyl with 1–6 C atoms, or $NR^4R^5$ is a 5- or 6-membered ring, optionally with other heteroatoms such as N, S, O, which ring may be substituted by A), and their physiologically acceptable salts.

Part of the invention also comprises the use of the medicaments as selective inhibitors of the cGMP-specific phosphodiesterases, and special embodiments of the invention comprise the use of the compounds of the general formula (I) and/or of the corresponding physiologically acceptable salts or of the above-mentioned medicaments for the production of medicament formulations for the treatment of disorders, in particular of the cardiovascular system and of heart failure, and pharmaceutical preparations which contain at least one of the above-mentioned compounds of the formula (I) and/or at least one of their physiological salts, or of the corresponding medicaments.

However, this invention also relates to pharmaceutical preparations, characterized in that they contain at least one compound of the above-mentioned formula (I) in which $R^1$, $R^2$ and $R^3$ have the above-mentioned meanings, and/or at least one of their physiological salts or of the corresponding medicaments acting as inhibitors, and are in a suitable dosage form together with at least one solid, liquid or semiliquid vehicle or auxiliary.

Part of the invention also comprises a process for the preparation of the compounds according to the above-mentioned formula (I) with the above-defined substituents $R^1$, $R^2$ and $R^3$ or of the corresponding inhibitors, characterized in that compounds of the general formula II

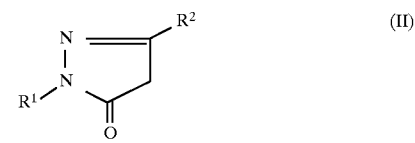

in which $R^1$ and $R^2$ have the above mentioned meanings, are reacted with suitable formaldehyde-donating compounds such as triazine or suitable trialkyl orthoformates, in particular trimethyl orthoformate, to give compounds of the general formula

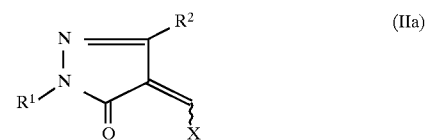

in which X is an amino or an —O-alkyl group (with 1–6 C atoms in the alkyl), and the latter are reacted, where appropriate in situ reacted, with suitable aniline derivatives of the formula III

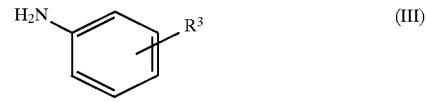

in which $R^3$ has the stated meanings, or their salts, where appropriate in suitable solvents, to give compounds of the formula I, and/or in that one or more radical(s) R in a compound of the formula I are converted into one or more other radicals R.

Compounds of the formula (I), mostly with different substituents, are disclosed as herbicidal and fungicidal agents in the Application EP-B1 0 274 642. It was therefore surprising to find that compounds of the formula I likewise act as selective inhibitors of cGMP-specific phosphodiesterase and can be used, inter alia, for the treatment of disorders of the cardiovascular system and of heart failure.

A particular advantage of the use of compounds according to the invention as pharmaceutically active substances is the very specific inhibition of cGMP phosphodiesterases (PDE V) while the inhibition which can be measured for phosphodiesterases PDE I, II, III and IV is more than ten thousand times less, that is to say negligible. Accordingly, when compounds which have such a specific action are used as medicaments there are no side effects which normally arise due to inhibition of the other phosphodiesterases.

Compounds of the formula II and their starting materials can be prepared by methods disclosed to the skilled person in numerous publications or slight modifications thereof. Appropriate methods are also described in the Patent EP-B1 0 274 642 or in the standard works such as Houben-Weyl "Methoden der organischen Chemie" [Methods of Organic Chemistry] Georg-Thieme-Verlag, Stuttgart, and are disclosed in the secondary literature indicated in the review handbook "Pyrazolones, Pyrazolidones, and Derivatives", Wiley, R. H., Wiley, P.; Interscience Publishers, John Wiley & Sons (1964) or described in the following articles: Ringel, C., Mayer, R., J. Prakt. Chem. 26 (1964) 333 ff; Gillespie, J. F.; Price, C. C., J. Org. Chem. 22 (1957) 780 ff; Tabel, K., Kawashima, E., Kato, T., Chem. Pharm. Bull. (CPBTAL), 29 (1) (1981), 244 ff; Wilson, J. D., Fulmer, T. D., Dasher, L. P., Beam, C. F., J. Heterocycl. Chem. 17 (2) (1980) 389–391; Neunhoefer, H., Koehler, G., Degen H.-J.; Liebigs Ann. Chem. (1985), N 1, 78–89 Ege, S., Adams, A. D., Gess, E. J., Ragone, K. S., Kober, B. J., J. Chem. Soc. Perkin Trans. (1983) N 2, 325–321; Pathak, R. B., Bahel, S. C., J. Indian Chem. Soc. 57 (1980) 1108–1111; Ali, M. I., El-Morsy, M. M. S., Hammouda H. A., Sharaf, M. F., Egypt. J. Chem. 22 (1979) 179–188; Mcevoy F. J., Albright J. D., J. Org. Chem. 44 (1979) 4597–4603.

In the subsequent reaction steps, compounds of the formula II are reacted further to give the compounds of the formula I according to the invention, which may be in the form of geometric isomers or mixtures of isomers of varying composition. This can either take place via an intermediate in which the 4 position of the pyrazoline ring is substituted by a methylene group, and subsequent reaction with an aniline derivative, or the substitution can take place directly by an appropriate aniline derivative. The choice of the variant of the preparation in this case is influenced by the chemical properties of the substituents of the pyrazolinone.

Some of the prepared compounds of the formula I can exist in tautomeric equilibrium:

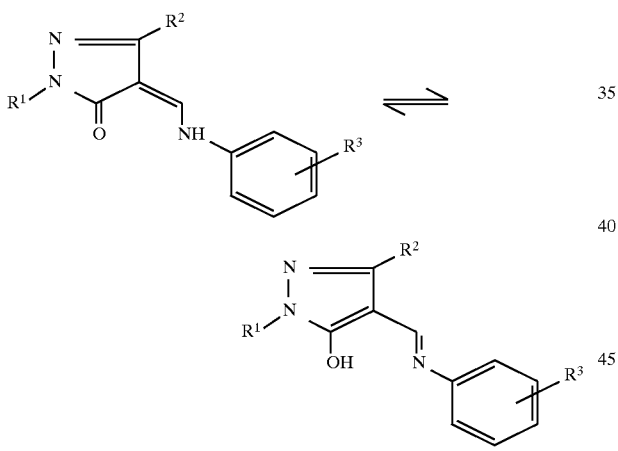

However, reference is always made to the use of compounds of the formula I although both the pure compounds and their mixtures with varying contents of the tautomeric or isomeric compounds are meant.

In particular, both the novel and the previously disclosed compounds of the formula I can be prepared by reacting compounds of the general formula IIa

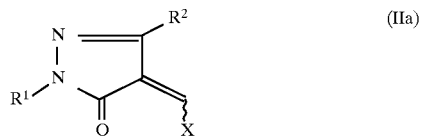

in which $R^1$ and $R^2$ have the above-mentioned meanings, and X can be an amino or alkoxy group, with suitable aniline derivatives of the formula III

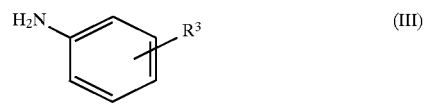

in which $R^3$ can have the above-mentioned meanings. This reaction is carried out where appropriate in the presence of a suitable diluent preferably at temperatures from 0° to 120° C., in particular at elevated temperatures.

Compounds of the formula IIa can be prepared by reacting suitable compounds of the general formula II

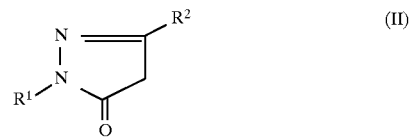

with formaldehyde-donating groups from the group of triazine, dimethylformamide, dimethylformamide dimethyl acetal, Gold's reagent, formyl chloride, formamide or alkyl derivatives of formamide with 1–6 C atoms in the alkyl or those from the group of trialkyl orthoformates, in particular trimethyl orthoformate. The reaction takes place where appropriate in a suitable diluent which does not interfere with subsequent use, such as, for example, glacial acetic acid, and possibly with a suitable catalyst. The compounds of the formula IIa can be isolated as intermediates. However, they can also be reacted further directly by reaction in situ with appropriate amnities of the fonuala :ill to give compounds, of the formula I.

Another synthetic route for the preparation of compounds of the formula I is particularly preferred when the compounds of the formula II have sensitive substituents which preferentially react in the reaction with formaldehyde-donating compounds or in the reaction with aniline derivatives of the formula III. In these cases, an appropriate aryl isocyanate is preferably reacted in a known manner in the presence of a base, in particular of butyl- or methyllithium, with the appropriate compound of the formula II.

Compounds of the general formula II are normally prepared by reacting b-keto esters or 1,3-dicarbonyl compounds of the general formula IV

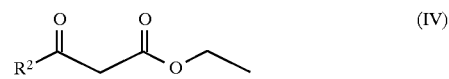

in which $R^2$ can have the above-mentioned meanings, with hydrazines of the general formula V

or their salts such as, for example, their hydrochlorides, hydrosulfates, hydrooxalates etc., where appropriate in the presence of a suitable diluent which proves not to interfere in the subsequent use of the reaction product, such as, for example, ethanol, and where appropriate in the presence of a suitable catalyst such as toluenesulfonic acid, at temperatures from about 0° to 120° C.

The 1,3-dicarbonyl compounds of the formula IV which are used are generally known compounds of organic chemistry and either are commercially available or can be synthesized by methods generally known to the skilled person.

The hydrazines required for carrying out the cyclization reaction are known compounds or can be obtained by methods generally known to the skilled person (see, for example, Houben-Weyl, Methoden der organischen Chemie, Vol. X, 2, page 203, Thieme Verlag Stuttgart 1967).

As already mentioned, compounds of the present invention have an above-average selectivity as inhibitors of cGMP PD esterases. Hence the cGMP concentration in the body is increased under the influence of these inhibitors. The effect of this is an advantageous increase in the inhibition of platelet aggregation, and an increase in granulocyte activity, vasospasm and an increasing vasodilating activity as well as a potentiation of the effect of endothelium-derived relaxing factor. Accordingly, the compounds can be used for the treatment of various disorders, including hypertension of varying severity, of heart failure of various causes, of arteriosclerosis, the consequences of narrowed blood vessels, for example in stroke, bronchitis, chronic and allergic asthma, allergic hayfever, glaucoma and disorders characterized by disturbances of the peristalsis of the digestive organs.

The biological activities of the compounds according to the present invention were determined by methods like those described, for example, in the international application WO-A1 93/06104.

Thus, the affinities of the compounds for cGMP and cAMP phosphodiesterases were determined by measuring their $IC_{50}$ values (concentration of the inhibitor required to achieve 50% inhibition of enzyme activity). The determinations were carried out using enzymes isolated by known methods (for example of: W. J. Thompson et al., Biochem, 1971, 10, 311). The tests were carried out using a modification of the batch method of W. J. Thompson and M. M. Appleman (Biochem., 1979, 18, 5228).

Results of these tests show that the compounds according to the general formula I are effective and selective inhibitors of cGMP phosphodiesterases. This particularly applies to those compounds according to the general formula I in which $R^2$ is a methyl, propyl, hydroxycarbonylmethyl or alkoxycarbonylmethyl radical and $R^1$ is benzoic acid, benzenesulfonic acid, N-methyl- or N,N-dialkylbenzenesulfonamide, acylaminophenyl, N,N-diethylbenzamide or benzamides.

Compounds according to the general formula I with the substituents methyl or propyl as $R^2$ and benzoic acid, benzamide, N-hexylbenzamide or N,N-diethylbenzamide, bensenesulfonamide or acylaminophenyl as $R^1$ display a particularly pronounced platelet aggregation-inhibiting action.

The compounds of the general formula I and their physiologically acceptable salts can therefore be used to produce pharmaceutical products by converting them together with at least one vehicle or auxiliary and, if required, with one or more other active substances into a suitable dosage form. The preparations obtained in this way can be used as medicaments in human or veterinary medicine. Suitable carrier substances are organic or inorganic substances which are suitable for enteral (for example oral or rectal) or parenteral administration or for administration in the form of an inhalation spray and which do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc or cellulose. Tablets, coated tablets, capsules, syrups, solutions or drops are used in particular for oral administration; specifically of interest are lacquered tablets and capsules with coatings and capsule shells, respectively, which are resistant to gastric fluid. Used for rectal administration are suppositories and for parenteral administration are solutions, preferably oily or aqueous solutions, furthermore suspensions, emulsions or implants. For administration as inhalation spray it is possible to use sprays which contain the active substance either dissolved or suspended in a propellant gas mixture (for example chlorofluorocarbons). In this case, the active substance is expediently used in micronized form, it being possible for one or more additional physiologically tolerated solvents to be present, for example ethanol. Inhalation solutions can be administered with the aid of conventional inhalers. The active substances claimed according to the invention can also be lyophilized, and the resulting lyophilizates can be used, for example, to produce injection products. The stated preparations can be sterilized and/or contain auxiliaries such as preservatives, stabilizers and/or wetting agents, emulsifiers, salts to influence the osmotic pressure, buffer substances, colorants and/or flavorings. They can, if required, also contain one or more other active substances, for example one or more vitamins, diuretics, antiinflammatory agents.

The compounds according to the formula I according to the invention may, in general, be administered in analogy to other known, commercially available products, but especially in analogy to the compounds described in U.S. Pat. No. 4,880,804, preferably in dosages from about 1 mg to 1 g, in particular from 50 to 500 mg, per dosage unit. The daily dosage is preferably from about 0.1 to 50 mg/kg, in particular from 1 to 10 mg/kg of body weight. The specific dose for each individual patient depends, however, on a wide variety of factors, for example on the activity of the specific compound used, on the age, body weight, general state of health, sex, on the diet, on the time and route of administration, on the rate of excretion, medicinal substance combination and severity of the particular disorder at which the therapy is directed. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 18 082.8, are hereby incorporated by reference.

Examples which serve to illustrate the invention are given below but do not limit the invention to the examples given.

In the following examples, "usual working up" means: if necessary, water is added, the pH is adjusted to values between 2 and 10 if necessary, depending on the constitution of the final product, extraction is carried out with ethyl acetate or dichloromethane, the organic phase is separated off, dried over sodium sulfate and evaporated, and purification is carried out by chromatography on silica gel and/or by crystallization. All temperatures hereinbefore and hereinafter are stated in °C.

EXAMPLES 1a) 5-Methyl-2-(4-nitrophenyl)-2,4-dihydro-3-pyrazolone (cyclization reaction)

1.63 g of p-nitrophenylhydrazine hydrochloride and 1.26 g of ethyl acetoacetate are heated under reflux in 30 ml of ethanol for 45 min. The mixture is concentrated somewhat in vacuo. The crystals which have separated out are then filtered off with suction.

Yield: 1.20 g of 5-methyl-2-(4-nitrophenyl)-2,4-dihydro-3-pyrazolone (64% of theory); Melting point: 223° C.

1b) 4-(2-Ethylphenylaminomethylene)-5-methyl-2-(4-nitrophenyl)-2,4-dihydro-3-pyrazolone (One-stage reaction: addition of formamide and aniline)

1 g of 5-methyl-2-(4-nitrophenyl)-2,4-dihydro-3-pyrazolone, 190 mg of 1,3,5-triazine and 0.74 ml of 2-ethylaniline are heated under reflux in 50 ml of ethanol for 4 days. The solvent is evaporated off in vacuo, and the crude reaction product obtained in this way is purified by chromatography on silica gel with a solvent mixture consisting of dichloromethane and methanol mixed in the ratio of 97:3 as eluent.

Yield: 1.33 g of 4-(2-ethylphenylaminomethylene)-5-methyl-2-(4-nitrophenyl)-2,4-dihydro-3-pyrazolone (83% of theory); Melting point: 220° C.

1 c) 3-Methyl-4-aminomethylene-1-phenyl-4,5-dihydro-5-pyrazolone (Formamide addition)

8.11 g (0.1 mol) of 1,3,5-triazine are added to a stirred suspension of 52.3 g (0.3 mol) of 3-methyl-1-phenyl-5-pyrazolinone in 800 ml of ethanol, and the mixture is boiled under reflux for one hour. The solution is then evaporated to a smaller volume in a rotary evaporator. The crystals which separate out during this are filtered off with suction in the cold. This results in 24.5 g of crystals from which 3-methyl-4-aminomethylene-1-phenyl-4,5-dihydro-5-pyrazolone is separated by chromatography on silica gel with a solvent mixture consisting of dichloromethane and acetone in the ratio 4:1 as eluent.

Evaporation of the mother liquor in a rotary evaporator results in 36 g of a resin from which 14.1 g of the dimeric compound (m.p.: 180.6° C.) are separated by chromatography in the same way. It is recrystallized from acetone.

1d) 3-Methyl-4-(2-propoxyphenylaminomethylene)-1-phenyl-4,5-dihydro-5-pyrazolone (Aniline addition)

2 g of 3-methyl-4-aminomethylene-1-phenyl-4,5-dihydro-5-pyrazolone and 1.6 g of 2-propoxyaniline trifluoroacetate are added to ethanol and boiled under reflux for 1.5 hours. The reaction solution is concentrated. The reaction product is then separated by chromatography on silica gel using a solvent mixture consisting of methyl butyl ketone/hexane 4:1 as eluent and is recrystallized from a methyl butyl ketone/hexane mixture.

Yield: 1.5 g of 3-methyl-4-(2-propoxyphenylaminomethylene)-1-phenyl-4,5-dihydro-5-pyrazolone (45.5% of theory); No dimeric product can be detected.

1e) 4-(2-Methoxyphenylaminomethylene)-5-methyl-2-phenyl-2,4-dihydro-3-pyrazolone 2 g of 5-methyl-2-phenyl-2,4-dihydro-3-pyrazolone, 188 ml of trimethyl orthoformate and 1.29 ml of o-anisidine are heated with stirring in 5 ml of glacial acetic acid at 70° C. for 2 h. The reaction mixture is cooled and 10 ml of methanol are added. The precipitate which has separated out is filtered off with suction and recrystallized from ethyl acetate.

Yield:1.1gof4-(2-methoxyphenylaminomethylene)-5-methyl-2-phenyl-2,4-dihydro-3-pyrazolone (31% of theory); Melting point: 143° C.

2a) 4-(4,5-Dihydro4-(2-ethylanilinomethylene)-3-methyl-5-oxo-1H-pyrazol-1-yl)-N-hexylbenzamide (Subsequent derivatization of the 1-substituent)

0.5 g (1.43 mmol) of 4-(4,5-dihydro-4-(2-ethylanilinomethylene)-3-methyl-5-oxo-1H-pyrazol-1-yl)-benzoic acid and 0.19 ml (1.43 mmol) of hexylamine and 20 ml of DMF are mixed together in a reaction flask and stirred for about 5 minutes at room temperature. Then, 0.27 g (1.43 mmol) of-N-(3-dimethylaminopropyl)-N'-ethylcarbodiimide HCl, 0.19 g (1.43 mmol) of 1-hydroxybenzotriazole and 0.18 ml (1.43 mmol) of N-methylmorpholine are successively added and the mixture is stirred at room temperature for 3 hours. Completion of the reaction is established by thin-layer chromatography (TLC in CH$_2$Cl$_2$/MeOH 9:1 (ninhydrin spray reagent)).

The reaction mixture is then taken up in 200 ml of water (no precipitate) and extracted twice with ethyl ether, the combined ether phases are dried over sodium sulfate and then filtered, the ether is removed by distillation in vacuo, and the residue obtained in this way is worked up by chromatography (column: silica gel Si6O, eluent: methyl butyl ether).

Yield: 250 mg of 4-(4,5-dihydro4-(2-ethylanilinomethylene)-3-methyl-5-oxo-1H-pyrazol-1-yl)-N-hexylbenzamide (41.6% of theory)

2b) 4-(2-Ethylanilinomethylene)-4,5-dihydro-3-methyl-1-(3-(1H-tetrazol-5-yl)phenyl)-1H-pyrazol-5-one (Subsequent derivatization of the 1-substituent)

200 mg (0.6 mmol) of 3-(4,5-dihydro-4-(2-ethylanilinomethylene)-3-methyl-5-oxo-1H-pyrazol-1-yl)-benzonitrile, 480 mg (2.4 mmol) of trimethyltin azide and 20 ml of toluene are mixed together and heated under reflux while stirring for two days. After this reaction time, small amounts of the precursors are still detectable by chromatography. The working up is carried out in the following way:

The precipitate which has formed during the reaction is filtered off with suction. This consists of product which is contaminated only by Sn salts. The product is therefore purified by chromatography (column: silica gel Si6O, eluent: CH$_2$Cl$_2$/MeOH 9:1).

Yield: 100 mg of 4-(2-ethylanilinomethylene)-4,5-dihydro-3-methyl-1-(3-(1H-tetrazol-5-yl)phenyl)-1H-pyrazol-5-one (45.5% of theory)

Apart from the compounds mentioned in Preparation Examples 1 and 2, the following specific 3-pyrazolone derivatives of the general formula I were prepared by the described processes using triazine or trimethyl orthoformate:

3. From 4-(4-morpholinylsulfonyl)phenylhydrazine and ethyl acetoacetate 5-methyl-2-(4-(4-morpholinylsulfonyl)phenyl)-2,4-dihydro-3-pyrazolone and 2-ethylaniline 4-(2-ethylanilinomethylene)-2,4-dihydro-5-methyl-2-(4-(4-morpholinylsulfonyl)phenyl)-3H-pyrazol-3-one. m.p.: 275° C.

4. From 3-acetamidophenylhydrazine and ethyl acetoacetate N-(3-(4,5-dihydro-3-methyl-5-oxo-5H-pyrazol-1-yl)-phenyl)acetamide and 2-ethylaniline N-(3-(4-(2-ethylanilinomethylene)-4,5-dihydro-3-methyl-5-oxo-5H-pyrazol-1-yl)phenyl)acetamide, m.p.: 263° C.

5. From N,N-diethyl-4-hydrazinobenzenesulfonamide and ethyl acetoacetate N,N-diethyl-4-(4,5-dihydro-3-methyl-5-oxo-1H-pyrazol-1-yl)benzenesulfonamide and 2-ethylaniline N,N-diethyl-4-(4-(2-ethylanilinomethylene)-4,5-dihydro-3-methyl-5-oxo-1H-pyrazol-1-yl) benzenesulfonamide, m.p.: 1940° C.

6. From N-ethyl-4-hydrazinobenzenesulfonamide and ethyl acetoacetate N-ethyl-4-(4,5-dihydro-3-methyl-5-oxo-1H-pyrazol-1-yl)benzenesulfonamide and 2-ethylaniline N-ethyl4-(4-(2-ethylanilinomethylene)-4,5-dihydro-3-methyl-5-oxo-1H-pyrazol-1-yl)benzenesulfonamide, m.p.: 260° C.

7. From 4-(4-morpholinylsulfonyl)phenylhydrazine and ethyl acetoacetate 5-methyl-2-(4-(4-morpholinylsulfonyl)phenyl)-2,4-dihydro-3-pyrazolone and 2-butoxyaniline 4-(2-butoxyanilinomethylene)-2,4-dihydro-5-methyl-2-(4-(4-morpholinylsulfonyl)phenyl)-3H-pyrazol-3-one, m.p.: 171° C.

8. From 4-(4-morpholinylsulfonyl)phenylhydrazine and ethyl acetoacetate 5-methyl-2-(4-(4-morpholinylsulfonyl)phenyl)-2,4-dihydro-3-pyrazolone and 2-ethoxyaniline 4-(2-ethoxyanilinomethylene)-2,4-dihydro-5-methyl-2-(4-(4-morpholinylsulfonyl)phenyl)-3H-pyrazol-3-one, m.p.: 265° C.

9. From 4-(4-methyl-1-piperazinylsulfonyl) phenylhydrazine and ethyl acetoacetate 5-methyl-2-(4-(4-methyl-1-piperazinylsulfonyl)-phenyl)-2,4-dihydro-3-pyrazolone and 2-ethylaniline 4-(2-ethylanilinomethylene)-2,4-dihydro-5-methyl-2-(4-(4-methyl-1-piperazinylsulfonyl)phenyl)-3H-pyrazol-3-one, m.p.: 254° C.

10a) 2-(3-Aminophenyl)-5-methyl-2,4-dihydro-3-pyrazolone (Hydrogenation of a substituent)

A solution consisting of 15 g of 5-methyl-2-(3-nitrophenyl)-2,4-dihydro-3-pyrazolone in 400 ml of methanol is hydrogenated in the presence of 10 g of Raney nickel. The catalyst is filtered off and the residue obtained after concentration of the solution in vacuo is recrystallized from isopropanol.

Yield: 8.0 g of 2-(3-aminophenyl)-5-methyl-2,4-dihydro-3-pyrazolone (62% of theory); Melting point: 265° C.

The following are obtained analogously from the corresponding nitro compounds:

2-(4-aminophenyl)-5-methyl-2,4-dihydro-3-pyrazolone (amorphous)

2-(2-aminophenyl)-5-methyl-2,4-dihydro-3-pyrazolone (amorphous)

10b) Reaction of the amino group of the N substituent of the pyrazole 2.2 ml of methanesulfonyl chloride are added to a stirred solution of 4.0 g of 2-(3-aminophenyl)-5-methyl-2,4-dihydro-3-pyrazolone in 30 ml of dichloromethane and 2 ml of pyridine while cooling in ice, and the mixture is then stirred for 2 hours. The solution is then washed with dilute hydrochloric acid and water, dried and concentrated in vacuo. From the resulting N-(3-(4,5-dihydro-3-methyl-5-oxo-1H-pyrazol-1-yl)phenyl)methanesulfon-amide and 2-ethyl aniline, N-(3-(4-(2-ethylanilino-methylene)-4,5-dihydro-3-methyl-5-oxo-1H-pyrazol-1-yl)phenyl) methanesulfonamide is obtained, m.p.: 192° C.

11. Reaction of the amino group of the N substituent of the pyrazole with methyl chloroformate or methanesulfonyl chloride 2.2 ml of methyl chloroformate are added to a stirred solution of 4.0 g of 2-(3-aminophenyl)-5-methyl-2,4-dihydro-3-pyrazolone in 30 ml of dichloromethane and 2 ml of pyridine while cooling in ice, and the mixture is stirred for 2 hours. The solution is then washed with dilute hydrochloric acid and water, dried and concentrated in vacuo.

Yield: 4.2 g of methyl N-(3-(4,5-dihydro-3-methyl-5-oxo-1H-pyrazol-1-yl)phenyl)carbamate (76% of theory), oil Further reaction with 2-ethylaniline of this compound leads to methyl N-(3-(4-(2-ethylanilino-methylene)-4,5-dihydro-3-methyl-5-oxo-1H-pyrazo-1-yl)-phenyl)-carbamate, m.p.: 229° C.

Obtained analogously from 2-(4-aminophenyl)-5-methyl-2,4-dihydro-3-pyrazolone and methanesulfonyl chloride is N-(4-(4,5-dihydro-3-methyl-5-oxo-1H-pyrazol-1-yl)phenyl)methanesulfonamide and from 2-(4-aminophenyl)-5-methyl-2,4-dihydro-3-pyrazolone and methyl chloroformate is methyl N-(4-(4,5-dihydro-3-methyl-5-oxo-1H-pyrazol-1-yl)phenyl)carbamate 12. N-(4-(4,5-Dihydro-3-methyl-5-oxo-1H-pyrazol-1-yl)-phel)acetamide (Reaction of the amino group of the N substituent of the pyrazole with acetic acid derivatives)

1.0 ml of acetic anhydride is added to 1.9 g of 2-(4-aminophenyl)-5-methyl-2,4-dihydro-3-pyrazolone in 40 ml of tetrahydrofiran while to stirring and cooling in ice, and the mixture is then stirred for 2 hours. The solution is concentrated in vacuo and the residue is worked up as usual.

Yield: 1.5 g of N-(4-(4,5-dihydro-3-methyl-5-oxo-1H-pyrazol-1-yl)phenyl)acetamide (65% of theory), oil obtained analogously from 2-(4-aminophenyl)-5-methyl-2,4-dihydro-3-pyrazolone and trifluoroacetic anhydride is N-(4-(4,5-dihydro-3-methyl-5-oxo-1H-pyrazol-1-yl)-phenyl)trifluoroacetamide from 2-(3-aminophenyl)-5-methyl-2,4-dihydro-3-pyrazolone and trifluoroacetic anhydride is N-(3-(4,5-dihydro-3-methy-5-oxo-1H-pyrazol-1-yl)-phenyl)trifluoroacetamide from 2-(3-aminophenyl)-5-methyl-2,4-dihydro-3-pyrazolone and acetic anhydride is N-(3-(4,5-dihydro-3-methyl-5-oxo-1H-pyrazol-1-yl)-phenyl)acetamide from 5-methyl-2-(4-aminophenyl)-2,4-dihydro-3-pyrazolone (prepared in analogy to Example 10) and acetic anhydride is N-(4-(4,5-dihydro-3-methyl-5-oxo-5H-pyrazol-1-yl)-phenyl)acetamide and by reaction with 2-ethylaniline N-(4-(4-(2-ethylanilinomethylene)-4,5-dihydro-3-methyl-5-oxo-1H-pyrazol-1-yl)phenyl) acetamide, m.p.: 230° C.

13. From 5-methyl-2-(4-aminophenyl)-2,4-dihydro-3-pyrazolone and methanesulfonyl chloride (reaction takes place as in Preparation Example 11 using the methanesulfonyl chloride in corresponding molar amount) is N-(4-(4,5-dihydro-3-methyl-5-oxo-1H-pyrazol-1-yl)-phenyl)-N-methylsulfonylmethanesulfonamide and 2-ethylaniline N-(4-(4-(2-ethylanilinomethylene)-4,5-dihydro-3-methyl-5-oxo-1H-pyrazol-1-yl)phenyl)-N-methylsulfonylmethanesulfonamide, m.p.: 268° C.

14. From 5-methyl-2-(2-aminophenyl)-2,4-dihydro-3-pyrazolone and methanesulfonyl chloride (reaction takes place as in Preparation Example 11) is N-(4-(4,5-dihydro-3-methyl-5-oxo-1H-pyrazol-1-yl)-phenyl) methanesulfonamide and 2-ethylaniline N-(2-(4-(2-ethylanilinomethylene)-4,5-dihydro-3-methyl-5-oxo-1H-pyrazol-1-yl)phenyl)methanesulfonamide, m.p.: 231° C.

15. From 5-methyl-2-(3-aminophenyl)-2,4-dihydro-3-pyrazolone and trifluoroacetic anhydride (reaction takes place as in Preparation Example 12) is N-(3-(4,5-dihydro-3-methyl-5-oxo-1H-pyrazol-5-yl)-phenyl) trifluoroacetamide and 2-ethylaniline N-(3-(4-(2-ethylanilinomethylene)-4,5-dihydro-3-methyl-5-oxo-1H-pyrazol-5-yl)phenyl)trifluoroacetamide, m.p.: 240° C.

16. From N,N-diethyl-4-hydrazinobenzenesulfonamide and ethyl acetoacetate is N,N-diethyl-4-(4,5-dihydro-3-methyl-5-oxo-1H-pyrazol-1-yl)benzenesulfonamide and 2-ethoxyaniline N,N-diethyl-4-(4,5-dihydro-4-(2-ethoxyanilinomethylene)-3-methyl-5-oxo-1H-pyrazol-1-yl) benzenesulfonamide, m.p.: 170° C.

17. From N,N-diethyl-4-hydrazinobenzenesulfonamide and ethyl acetoacetate N,N-diethyi-4-(4,5-dihydro-3-methyl-5-oxo-1H-pyrazol-1-yl)benzenesulfonamide and 2-methoxyaniline N,N-diethyl-4-(4,5-dihydro-4-(2-methoxyanilinomethylene)-3-methyl-5-oxo-1H-pyrazol-1-yl)benzenesulfonamide, m.p.: 191° C.

18. From N-ethyl-4-hydrazinobenzenesulfonamide and ethyl acetoacetate is N-ethyl-4-(4,5-dihyro-3-methyl-5-oxo-1H-pyrazol-1-yl)benzenesulfonamide and 2-ethoxyaniline 4-((2-ethoxyanilinomethylene)-4,5-dihydro-3-methyl-5-oxo-1H-pyrazol-1-yl)-N-ethylbenzenesulfonamide, m.p.: 238° C.

19. From 5-methyl-2-(4-aminophenyl)-2,4-dihydro-3-pyrazolone and ethyl chloroformate (as in Preparation Example 11) is ethyl N-(4-(4,5-dihydro-3-methyl-5-oxo-1H-pyrazol-1-yl)phenyl)carbamate and 2-methoxyaniline ethyl N-(4-(4,5-dihydro-4-(2-methoxyanilinomethylene)-3-methyl-5-oxo-1H-pyrazol-1-yl)phenyl)-carbamate, m.p.: 212° C.

20. From 5-methyl-2-(4-aminophenyl)-2,4-dihydro-3-pyrazolone and propionyl chloride (as in Preparation Example 11) is N-(4-(4,5-dihydro-3-methyl-5-oxo-1H-pyrazol-1-yl)-phenyl)propionamide and 2-ethoxyaniline N-(4-(4-(2-ethoxyanilinomethylene)-4,5-dihydro-3-methyl-5-oxo-1H-pyrazol-1-yl)phenyl)propionamide, m.p.: 208° C.

21. From 4-(1-piperidylsulfonyl)phenylhydrazine and ethyl acetoacetate is 5-methyl-2-(4-(1-piperidylsulfonyl)phenyl)-3H-pyrazol-3-one and 2-ethoxyaniline 4-(2-ethoxyanilinomethylene)-2,4-dihydro-5-methyl-2-(4-(1-piperidylsulfonyl)phenyl)-3H-pyrazol-3-one, m.p.: 252° C.

22. From N-tert-butyl-4-hydrazinobenzenesulfonamide and ethyl butyrylacetate is N-tert-butyl-4-(4,5-dihydro-3-propyl-5-oxo-1H-pyrazol-1-yl)benzenesulfonamide and 2-ethoxyaniline N-tert-butyl-4-(4-(2-ethoxyanilinomethylene)-4,5-dihydro-3-propyl-5-oxo-1H-pyrazol-1-yl)benzenesulfonamide, m.p.: 254° C.

23. N-Acetyl-4-(4-(2-ethoxyanilinomethylene)-4,5-dihydro-3-methyl-5-oxo-1H-pyrazol-1-yl)benzenesulfonamide (Derivatization of the N substituent of the pyrazole after the aniline derivative has been condensed on)

0.17 ml of acetic anhydride is added dropwise to a solution of 1.0 g of 4-(4-(2-ethoxyanilinomethylene)-4,5-dihydro-3-methyl-5-oxo-1H-pyrazol-1-yl)benzenesulfonamide and 0.9 g of dimethylaminopyridine in 30 ml of pyridine while cooling in ice, and the mixture is then stirred for 10 hours. The residue obtained after concentration in vacuo is mixed with dilute hydrochloric acid, and the crystals which have separated out are filtered off with suction and triturated with ethanol.

Yield: 0.47 g of N-acetyl-4-(4-(2-ethoxyanilinomethylene)-4,5-dihydro-3-methyl-5-oxo-1H-pyrazol-1-yl)benzenesulfonamide (42.5% of theory) Melting point: 282° C.

24. From 4-hydrazinobenzenesulfonamide and ethyl acetoacetate 4-(4,5-dihydro-3-methyl-5-oxo-1H-pyrazol-1-yl)-benzenesulfonamide and 2-ethoxyaniline 4-(4-(2-ethoxyanilinomethylene)-4,5-dihydro-3-methyl-5-oxo-1H-pyrazol-1-yl)benzenesulfonamide, m.p.: 241° C.

25. From phenylhydrazine and methyl 5-hydroxy-3-oxopentanoate 5-(2-hydroxyethyl)-2-phenyl-2,4-dihydro-3-pyrazolone and 2-ethylaniline 4-(2-ethylanilinomethylene)-2,4-dihydro-5-(2-hydroxyethyl)-2-phenyl-1H-pyrazol-3-one 26. From 4-methoxybenzylhydrazine and ethyl butyrylacetate 2,4-dihdyro-2-(4-methoxybenzyl)-5-propyl-3H-pyrazol-3-one and 2-ethylaniline 4-(2-ethylanilinomethylene)-2,4-dihydro-2-(4-methoxybenzyl)-5-propyl-3H-pyrazol-3-one, oil 27. From 2-propoxybenzylhydrazine and ethyl butyrylacetate 2,4-dihydro-2-(2-propoxybenzyl)-5-propyl-3H-pyrazol-3-one and 2-ethylaniline 4-(2-ethylanilinomethylene)-2,4-dihydro-2-(2-propoxybenzyl)-5-propyl-3H-pyrazol-3-one, m.p.: 75.2° C.

28. From 4-bromophenylhydrazine and ethyl butyrylacetate 2-(4-bromophenyl)-2,4-dihydro-5-propyl-3H-pyrazol-3-one and 2-ethylaniline 2-(4-bromophenyl)4-(2-ethylanilinomethylene)-2,4-dihydro-5-propyl-3H-pyrazol-3-one, m.p.: 126.9° C.

29. From 4-nitrophenylhydrazine and ethyl butyrylacetate 2,4-dihydro-2-(4-nitrophenyl)-5-propyl-3H-pyrazol-3-one and 2-ethylaniline 4-(2-ethylanilinomethylene)-2,4-dihydro-2-(4-nitrophenyl)-5-propyl-3H-pyrazol-3-one, m.p.: 211° C.

30. From 3-hydrazinobenzenesulfonic acid and ethyl butyrylacetate 3-(4,5-dihydro-5-oxo-3-propyl-1H-pyrazol-1-yl)-benzenesulfonic acid and 2-ethylaniline 3-(4-(2-ethylanilinomethylene)-4,5-dihydro-5-oxo-3-propyl-1H-pyrazol-1-yl)benzenesulfonic acid, m.p.: 258.6° C.

31. From 4-hydrazinobenzenesulfonic acid and ethyl butyrylacetate 4-(4,5-dihydro-5-oxo-3-propyl-1H-pyrazol-1-yl)-benzenesulfonic acid and 2-ethylaniline 4-(4-(2-ethylanilinomethylene)4,5-dihydro-5-oxo-3-propyl-1H-pyrazol-1-yl)benzenesulfonic acid, m.p.: 205.2° C.

32. From 4-nitrophenylhydrazine and diethyl 3-oxoglutarate Ethyl 2-(4,5-dihydro-1-(4-nitrophenyl)-5-oxo-1H-pyrazol-3-yl)acetate and 2-ethylaniline Ethyl 2-(4-(2-ethylanilinomethylene)-4,5-dihydro-1-(4-nitrophenyl)-5-oxo-1H-pyrazol-3-yl)acetate, m.p.: 224.5° C.

33. From 4-hydrazinobenzoic acid and ethyl acetoacetate 4-(4,5-dihydro-5-oxo-3-methyl-1H-pyrazol-1-yl)-benzoic acid and 2-ethylaniline 4-(4-(2-ethylanilinomethylene)-4,5-dihydro-5-oxo-3-methyl-1H-pyrazol-1-yl)benzoic acid, m.p.: 291° C.

34. From 2-pyridylhydrazine and ethyl butyrylacetate 2,4-dihydro-2-(2-pyridyl)-5-propyl-3H-pyrazol-3-one and 2-ethylaniline 4-(2-ethylanilinomethylene)-2,4-dihydro-2-(2-pyridyl)-5-propyl-3H-pyrazol-3-one, m.p.: 151° C.

35. From 2-pyridylhydrazine and ethyl acetoacetate 2,4-dihydro-5-methyl-2-(2-pyridyl)-3H-pyrazol-3-one and 2-ethylaniline 4-(2-ethylanilinomethylene)-2,4-dihydro-5-methyl-2-(2-pyridyl)-3H-pyrazol-3-one, m.p.: 182.9° C.

36. From 4-hydrazinobenzoic acid and ethyl butyrylacetate 4-(4,5-dihydro-5-oxo-3-propyl-1H-pyrazol-1-yl)-benzoic acid and 2-ethylaniline 4-(4-(2-ethylanilinomethylene)-4,5-dihydro-5-oxo-3-propyl-1H-pyrazol-1-yl)benzoic acid, m.p.: 254.5° C.

37. From 4-(4-(2-ethylanilinomethylene)-4,5-dihydro-3-methyl-5-oxo-1H-pyrazol-1-yl)benzoic acid and hexylamine 4-(4-(2-ethylanilinomethylene)-4,5 -dihydro-3-methyl-5-oxo-1H-pyrazol-1-yl)hexylbenzamide, m.p.: 62.1° C.

38. From 4-(4-(2-ethylanilinomethylene)-4,5-dihydro-3-methyl-5-oxo-1H-pyrazol-1-yl)benzoic acid and aqueous ammonia solution 4-(4-(2-ethylanilinomethylene)-4,5-dihydro-3-methyl-5-oxo-1H-pyrazol-1-yl)benzamide, m.p.: 225.2° C.

39. From 4-(4-(2-ethylanilinomethylene)-4,5-dihydro-3-methyl-5-oxo-1H-pyrazol-1-yl)benzoic acid and aqueous N,N-diethylamine solution N,N-diethyl-4-(4-(2-ethylanilinomethylene)-4,5-dihydro-3-methyl-5-oxo-1H-pyrazol-1-yl)benzamide, m.p.: 112° C.

40. From 4-pyridylhydrazine and ethyl butyrylacetate 2,4-dihydro-5-propyl-2-(4-pyridyl)-3H-pyrazol-3-one and 2-ethylaniline 4-(2-ethylanilinomethylene)-2,4-dihydro-5-propyl-2-(4-pyridyl)-3H-pyrazol-3-one, m.p.: 159.2° C.

41. From 4-chlorophenylhydrazine and ethyl acetoacetate 2-(4-chlorophenyl)-2,4-dihydro-5-methyl-3H-pyrazol-3-one and 2-ethylaniline 2-(4-chlorophenyl)-4-(2-ethylanilinomethylene)-2,4-dihydro-5-methyl-3H-pyrazol-3-one 42. From 4-(4-(2-ethylanilinomethylene)-4,5-dihydro-5-oxo-3-propyl-1H-pyrazol-1-yl)benzoic acid and aqueous diethylamine solution N,N-diethyl-4-(4-(2-ethylanilinomethylene)-4,5-dihydro-5-oxo-3-propyl-1H-pyrazol-1-yl)benzamide, m.p.: 123° C.

43. From 4-(4-(2-ethylanilinomethylene)-4,5-dihydro-5-oxo-3-propyl-1H-pyrazol-1-yl)benzoic acid and hexylamine 4-(4-(2-ethylanilinomethylene)-4,5-dihydro-5-oxo-3-propyl-1H-pyrazol-1-yl)-N-hexylbenzamide, m.p.: 46.7° C.

44. From 4-(4-(2-ethylanilinomethylene)-4,5-dihydro-5-oxo-3-propyl-1H-pyrazol-1-yl)benzoic acid and aqueous ammonia solution 4-(4-(2-ethylanilinomethylene)4,5-dihydro-5-oxo-3-propyl-1H-pyrazol-1-yl)benzamide, m.p.: 170° C.

45. From 4-hydrazinobenzonitrile and ethyl butyrylacetate 4-(4,5-dihydro-5-oxo-3-propyl-1H-pyrazol-1-yl)benzonitrile and 2-ethylaniline 4-(4-(2-ethylanilinomethylene)4,5-dihydro-5-oxo-3-propyl-1H-pyrazol-1-yl)benzonitrile, m.p.: 196.7° C.

46. From N,N-diethyl-3-hydrazino-4-methoxybenzenesulfonamide and ethyl butyrylacetate N,N-diethyl-3-(4,5-dihydro-5-oxo-3-propyl-1H-pyrazol-1-yl)-4-methoxybenzenesulfonamide and 2-ethylaniline N,N-diethyl-3-(4-(2-ethylanilinomethylene)-4,5-dihydro-5-oxo3-propyl-1H-pyrazol-1-yl)-4-methoxybenzenesulfonamide, oil 47. From 3-hydrazinobenzonitrile and ethyl acetoacetate 3-(4,5-dihydro-3-methyl-5-oxo-1H-pyrazol-1-yl)-benzonitrile and 2-ethylaniline 3-(4-(2-ethylanilinomethylene)-4,5-dihydro-3-methyl-5-oxo-1H-pyrazol-1-yl)benzonitrile, m.p.: 210.8° C.

48. From N-hexyl-3-hydrazino-4-propoxybenzenesulfonamide and ethyl acetoacetate 3-(4,5-dihydro-3-methyl-5-oxo-1H-pyrazol-1-ylmethyl)-N-hexyl-4-propoxybenzenesulfonamide and 2-ethylaniline 3-(4-(2-ethylanilinomethylene)-4,5-dihydro-3-methyl-5-oxo-1H-pyrazol-1-ylmethyl)-N-hexyl-4-propoxybenzenesulfonamide, resin 49. From 2-hydrazinobenzoic acid and ethyl butyrylacetate 2-(4,5-dihydro-5-oxo-3-propyl-1H-pyrazol-1-yl)-benzoic acid and 2-ethylaniline 2-(4-(2-ethylanilinomethylene)-4,5-dihydro-5-oxo-3-propyl-1H-pyrazol-1-yl)benzoic acid, m.p.: 126.9° C.

50. From 4-(4-(2-ethylanilinomethylene)-4,5-dihydro-5-oxo-3-propyl-1H-pyrazol-1-yl)benzonitrile and trimethyltin azide 4-(2-ethylanilinomethylene)-2,4-dihydro-5-propyl-2-(4-(1H-tetrazol-5-yl)phenyl-3H-pyrazol-3-one, m.p.: 248.5° C.

51. From 3-pyridylhydrazine and ethyl butyrylacetate 2,4-dihydro-5-propyl-2-(3-pyridyl)-3H-pyrazol-3-one and 2-ethylaniline 4-(2-ethylanilinomethylene)-2,4-dihydro-5-propyl-2-(3-pyridyl)-3H-pyrazol-3-one, m.p.: 143.9° C.

52. From 3-(4-(2-ethylanilinomethylene)-4,5-dihydro-3-methyl-5-oxo-1H-pyrazol-1-yl)benzonitrile and trimethyltin azide 4-(2-ethylanilinomethylene)-2,4-dihydro-5-methyl-2-(3-(1H-tetrazol-5-yl)phenyl-3H-pyrazol-3-one, m.p.: 261.6° C.

53. From hydrazinobenzoic acid and ethyl acetoacetate 4-(4,5-dihydro-3-methyl-5-oxo-1H-pyrazol-1-yl)-benzoic acid and 2-trifluoromethylaniline 4-(4,5-dihydro-3-methyl-5-oxo-4-(2-trifluoromethylanilinomethylene)-1H-pyrazol-1-yl)benzoic acid, m.p.: 289.4° C.

54. From p-hydrazinobenzoic acid and diethyl 3-oxoglutarate 4-(3-ethoxycarbonylmethyl-4,5-dihydro-5-oxo-1H-pyrazol-1-yl)benzoic acid and 2-ethylaniline 4-(4-(2-ethylanilinomethylene)-3-ethoxycarbonylmethyl-4,5-dihydro-5-oxo-1H-pyrazol-1-yl)benzoic acid, m.p.: 246° C.

55. From p-hydrazinobenzoic acid and ethyl acetoacetate 4-(4,5-dihydro-3-methyl-5-oxo-1H-pyrazol-1-yl)-benzoic acid and 2-(2-propynyloxy)aniline 4-(4,5-dihydro-3-methyl-5-oxo-4-(2-(2-propynyloxy)-anilinomethylene)-1H-pyrazol-1-yl)benzoic acid, m.p.: 267.9° C.

56. From p-hydrazinobenzoic acid and ethyl acetoacetate 4-(4,5-dihydro-3-methyl-5-oxo-1H-pyrazol-1-yl)-benzoic acid and 2-propoxyaniline 4-(4,5-dihydro-3-methyl-5-oxo-4-(2-propoxyanilinomethylene)-1H-pyrazol-1-yl)benzoic acid, m.p.: 259.6° C.

57. From p-hydrazinobenzoic acid and ethyl acetoacetate 4-(4,5-dihydro-3-methyl-5-oxo-1H-pyrazol-1-yl)-benzoic acid and 2-(2-propenyloxy)aniline 4-(4,5-dihydro-3-methyl-5-oxo-4-(2-(2-propenyloxy)-anilinomethylene)-1H-pyrazol-1-yl)benzoic acid, m.p.: 240.4° C.

58. From p-hydrazinobenzoic acid and ethyl acetoacetate 4-(4,5-dihydro-3-methyl-5-oxo-1H-pyrazol-1-yl)-benzoic acid and 2-methoxyaniline 4-(4,5-dihydro-4-(2-methoxyanilinomethylene)-3-methyl-5-oxo-1H-pyrazol-1-yl)benzoic acid, m.p.: >300° C.

59. From p-hydrazinobenzoic acid and ethyl acetoacetate 4-(4,5-dihydro-3-methyl-5-oxo-1H-pyrazol-1-yl)-benzoic acid and 2-isopropylaniline 4-(4,5-dihydro-4-(2-isopropylanilinomethylene)-3-methyl-5-oxo-1H-pyrazol-1-yl)benzoic acid, m.p.: 269.5° C.

60. From 3-(4,5-dihydro-3-methyl-5-oxo-1H-pyrazol-1-yl)-benzenesulfonamide, which can be bought, and 2-ethylaniline 3-(4-(2-ethylanilinomethyleneaminomethylene)-4,5-dihydro-3-methyl-5-oxo-1H-pyrazol-1-yl)benzenesulfonamide m.p.: 229.2° C.

61. From ethyl 2-(1-(4-aminophenyl)-4,5-dihydro-5-oxo-1H-pyrazol-3-yl)acetate and trifluoroacetic anhydride and subsequent reaction with ethylaniline ethyl 2-(4-(2-ethylanilinomethylene)-4,5-dihydro-1-(4-trifluoroacetamidophenyl)-5-oxo-1H-pyrazol-3-yl)-acetate, m.p.: 197° C.

62. From ethyl 2-(1-(4-aminophenyl)-4,5-dihydro-5-oxo-1H-pyrazol-3-yl)acetate and methyl chloroformate and subsequent reaction with 2-ethylaniline Ethyl 2-(1-(4-methoxycarbonylaminophenyl)-4-(2-ethylanilinomethylene)-4,5-dihydro-5-oxo-1H-pyrazol-3-yl)acetate, m.p.: 145° C.

63. From ethyl 2-(4,5-dihydro-1-(4-aminophenyl)-5-oxo-1H-pyrazol-3-yl)acetate and methanesulfonyl chloride and subsequent reaction with 2-ethylaniline ethyl 2-(4-(2-ethylanilinomethylene)-4,5-dihydro-1-(4-methanesulfonamidophenyl)-5-oxo-1H-pyrazol-3-yl)acetate,m. p. :165° C.

64. From ethyl 2-(4,5-dihydro-1-(4-aminophenyl)-5-oxo-1H-pyrazol-3-yl)acetate and acetyl chloride and subsequent reaction with 2-ethylaniline; ethyl 2-(1-(4-acetamidophenyl)-4-(2-ethylanilinomethylene)-4,5-dihydro-5-oxo-1H-pyrazol-3-yl)-acetate, m.p.: 197° C.

Other prepared compounds are:

ethyl 2-(1-(4-(N,N-diethylsulfamoyl)-phenyl)-4-(2-ethylanilinomethylene)-4,5-dihydro-5-oxo-1H-pyrazol-3-yl)-acetate, m.p.: 146° C.

ethyl 2-(1-(4-(N,N-diethylsulfamoyl)-phenyl)-4-(2-ethoxyanilinomethylene)-4,5-dihydro-5-oxo-1H-pyrazol-3-yl)-acetate, m.p.:127° C.

ethyl 2-(1-(4-acetamidophenyl)-4-(2-ethylanilinomethylene)-4,5-dihydro-5-oxo-1H-pyrazol-3-yl)-acetate, m.p.: 194° C.

ethyl 2-(4-(2-ethylanilinomethylene)-4,5-dihydro-5-oxo-1-(4-trifluoroacetamidophenyl)1H-pyrazol-3-yl)-acetate, m.p.: 197° C.

ethyl 2-(4-(2-ethylanilinomethylene)-4,5-dihydro-1-(4-methoxycarbonylaminophenyl)-5-oxo-1H-pyrazol-3-yl)-acetate, m. p.: 144° C.

ethyl 2-(4-(2-ethylanilinomethylene)-4,5-dihydro-1-(4-methanesulfonamidophenyl)-5-oxo-1H-pyrazol-3-yl)-acetate, m.p.: 165° C.

ethyl 2-(1-(4-acetamidophenyl)-4-(2-ethylanilinomethylene)-4,5-dihydro-5-oxo-1H-pyrazol-3-yl)-acetate, m.p.: 168° C.

2-(4-(2-ethylanilinomethylene)-4,5-dihydro-1-(4-methoxycarbonylaminophenyl)-5-oxo-1H-pyrazol-3-yl)-acetic acid, m.p.: 181° C.

N-(3-(4-(2-ethylanilinomethylene)-4,5-dihydro-5-oxo-3-propyl-1H-pyrazol-1-yl)-phenyl)-methanesulfonamide, m.p.: 214° C.

N-(3-(4-(2-ethylanilinomethylene)-4,5-dihydro-5-oxo-3-propyl-1H-pyrazol-1-yl)-phenyl)acetamide, m.p.: 181° C.

methyl N-(3-(4-(2-ethylanilinomethylene)-4,5-dihydro-5-oxo-3-propyl-1H-pyrazol-1-yl)-phenyl)-carbamate, m.p.:203° C.

ethyl 2-(4-(2-ethylanilinomethylene)-4,5-dihydro-5-oxo-1-(3-trifluoroacetamidophenyl)-1H-pyrazol-1-yl)-acetate, m.p. 190° C.

ethyl 2-(4-(2-ethylanilinomethylene)-4,5-dihydro-1-(3-methanesulfonamidophenyl)-5-oxo-1H-pyrazol-3-yl)-acetate, m.p.:174° C.

The following examples relate to pharmaceutical preparations:

EXAMPLE A

Vials

A solution of 100 g of an active substance of the formula I and 5 g of disodium hydrogen phosphate in 3 l of double-distilled water is adjusted to pH 6.5 with 2N hydrochloric acid, filtered sterile, dispensed into vials, lyophilized under sterile conditions and sealed sterile. Each vial contains 5 mg of active substance.

EXAMPLE B

Suppositories

A mixture of 20 g of an active substance of the formula I with 100 g of soya lecithin and 1400 g of cocoa butter is melted, poured into moulds and left to cool. Each suppository contains 20 mg of active substance.

EXAMPLE C

Solution

A solution is prepared from 1 g of an active substance of the formula I, 9.38 g of $NaH_2PO_4.2H_2O$, 28.48 g of $Na_2HPO_4.12H_2O$ and 0.1 g of benzalkonium chloride in 940 ml of double-distilled water. The solution is adjusted to pH 6.8, made up to 1 l and sterilized by radiation. This solution can be used in the form of eyedrops.

EXAMPLE D

Ointment 500 mg of an active substance of the formula I are mixed with 99.5 g of petrolatum under aseptic conditions.

EXAMPLE E

Tablets

A mixture of 1 kg of active substance of the formula I, 4 kg of lactose, 1.2 kg of potato starch, 0.2 kg of talc and 0.1 kg of magnesium stearate is compressed to tablets in a conventional way such that each tablet contains 10 mg of active substance.

EXAMPLE F

Coated tablets

Tablets are compressed in analogy to Example E and are then coated in a conventional way with a coating of sucrose, potato starch, talc, tragacanth and colorant.

EXAMPLE G

Capsules 2 kg of active substance of the formula I are packed in hard gelatin capsules in a conventional way so that each capsule contains 20 mg of the active substance.

EXAMPLE H

Ampoules

A solution of 1 kg of active substance of the formula I in 60 l of double-distilled water is filtered sterile, dispensed into ampoules, lyophilized under sterile conditions and sealed sterile. Each ampoule contains 10 mg of active substance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising a compound of the formula (I):

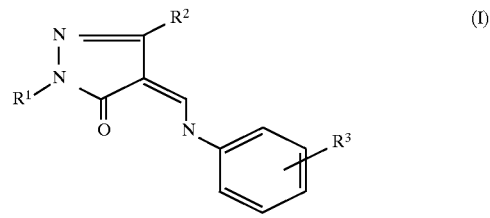

in which $R^1$ is benzyl; alkoxybenzyl with 1–3 C atoms in the alkoxy moiety; phenyl; phenyl which is substituted once to three times by amino, cyano, halogen, nitro, carboxyl, carbamoyl, N-alkylcarbamoyl, N,N-dialkylcarbamoyl with 1–6 C atoms in each alkyl moiety, A—O—CO—, A—CO—NH—, A—CO—NA—, $HSO_3$, $SO_2NR^4R^5$ (where $R^4$ and $R^5$ are independently H or alkyl with 1–6 C atoms or $NR^4R^5$ is a 5- or 6-membered ring optionally with other heteroatoms N, S or O which is optionally substituted on the ring by A), A—CO—NH—$SO_2$—, A—CO—NA—$SO_2$—, A—$SO_2$—NH—, A—$SO_2$—NA—, A—CO—$SO_2$—NH—, A—CO—$SO_2$—NA—, tetrazolyl or phospho; or pyridyl;

$R^2$ is hydroxyalkyl;

$R^3$ is H, straight-chain or branched alkyl with 1–5 C atoms, straight-chain or branched alkoxy with 1–5 C atoms, fluorine- or chlorine-substituted alkyl; and A is straight or branched alkyl with 1–6 C atoms or straight or branched fluorine- or chlorine substituted alkyl with 1–6 C atoms, or a salt thereof, and a pharmaceutically acceptable solid, liquid or semi-liquid vehicle or auxilliary in a form suitable for administration as a medicament in human or veterinary medicine.

2. The composition of claim 1, which further comprises a vitamin, diuretic or anti-inflammatory agent.

3. A method for treatment or control of a disease associated with cGMP phosphodiesterase activity which comprises administering to a patient a cGMP phosphodiesterase inhibiting effective amount of a pharmaceutical composition containing a compound of the formula (I):

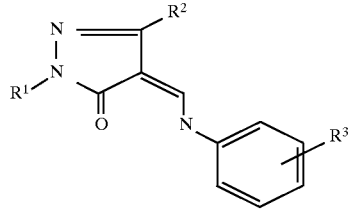

in which

R¹ is benzyl; alkoxybenzyl with 1–3 C atoms in the alkoxy moiety; phenyl; phenyl which is substituted once to three times by amino, cyano, halogen, nitro, A—CO—, carboxyl, AO—, carbamoyl, N-alkylcarbamoyl, N,N-dialkylcarbamoyl with 1–6 C atoms in each alkyl moiety, A—O—CO—, A—O—CO—NH—, A—O—CO—NA—, A—CO—NH—, A—CO—NA—, HSO₃—, A—SO₂—, SO₂NR⁴R⁵ (where R⁴ and R⁵ are independently H or alkyl with 1–6 C atoms or NR⁴R⁵ is a 5- or 6-membered ring optionally with other heteroatoms N, S or O which is optionally substituted on the ring by A), A—CO—NH—SO₂—, A—CO—NA—SO₂—, A—SO₂—NH—, A—SO₂—NA—, (A—SO₂—)₂N—, A—CO—SO₂—NH—, A—CO—SO₂—NA—, tetrazolyl or phospho; or pyridyl;

R² is alkyl, alkoxycarbonylalkyl, hydroxyalkyl or hydroxycarbonylalkyl;

R³ is H, straight-chain or branched alkyl, straight-chain or branched alkoxy, fluorine- or chlorine-substituted alkyl, aminoalkyl, aminoalkanoyl, SO₂NR⁴R⁵ where R⁴ and R⁵ are independently H or alkyl with 1–6 C atoms or NR⁴R⁵ is a 5- or 6-membered ring optionally with other heteroatoms N, S or O which ring is optionally substituted by A;

A is straight or branched alkyl with 1–6 C atoms or straight or branched flourine- or chlorine substituted alkyl with 1–6 C atoms, or a salt thereof.

4. The method of claim 3, wherein in the compound of the formula I

R¹ is benzyl; alkoxybenzyl with 1–3 C atoms in the alkoxy moiety; phenyl; phenyl which is substituted once to three times by amino, halogen, nitro, HSO₃—, cyano, carboxyl, A—O—CO—, A—CO—NH—, A—CO—NA—, carbamoyl, N-alkylcarbamoyl, N,N-dialkylcarbamoyl with 1–6 C atoms in each alkyl moiety, A—SO₂—NH—, A—SO₂—NA—, SO₂NR⁴R⁵ (where R⁴ and R⁵ are independently H or alkyl with 1–6 C atoms or NR⁴R⁵ is a 5- or 6-membered ring, optionally with other heteroatoms N, S or O which ring is optionally substituted by A), A—CO—NH—SO₂—, A—CO—NA—SO₂—, acylsulfonamido, tetrazolyl or phospho; or pyridyl;

R² is hydroxyalkyl; and

R³ is H, straight-chain or branched alkyl with 1–5 C atoms, straight-chain or branched alkoxy with 1–5 C atoms, fluorine- or chlorine-substituted alkyl, and A is as defined in claim 1, or a salt thereof.

5. The method of claim 3, wherein in the compound of the formula I

R¹ is benzyl; alkoxybenzyl with 1–3 C atoms in the alkoxy moiety; phenyl; phenyl which is substituted once to three times by A—CO—NH—, A—CO—NA—, N-alkylcarbamoyl, N,N-dialkylcarbamoyl with 1–6 C atoms in each alkyl moiety, A—CO—NH—SO₂—, A—CO—NA—SO₂—, A—CO—NA—, A—CO—NH—, HSO₃—, SO₂NR⁴R⁵ (where R⁴ and R⁵ are independently H or alkyl with 1–6 C atoms or NR⁴R⁵ is a 5- or 6-membered ring, optionally with other heteroatoms N, S or O which ring is optionally substituted by A), tetrazolyl or phospho; or pyridyl;

R² is H₃C—O—CO—CH₂—; and

R³ is aminoalkyl, aminoalkanoyl, SO₂NR⁴R⁵ where R⁴ and R⁵ are independently H or alkyl with 1–6 C atoms or NR⁴R⁵ is a 5- or 6-membered ring optionally with other heteroatoms N, S or O which ring is optionally substituted by A; and A is as defined in claim 1, or a salt thereof.

6. The method of claim 3, wherein the disease is treated or controlled by selective inhibition of cGMP-specific phosphodiesterase.

7. The method of claim 3, wherein the disease is a disorder of the cardiovascular system, heart failure or both.

8. The method of claim 3, wherein the compound of the formula (I) is 4-(4-(2-ethylanilinomethylene)-4,5-dihydro-5-oxo-3-methyl-1H-pyrazol-1-yl)benzoic acid.

9. The method of claim 3, wherein the compound of the formula (I) is administered in a daily dosage of from 0.1 to 50 mg/kg of body weight.

10. The method of claim 3, wherein the compound of the formula (I) is administered in a daily dosage of from 1 to 10 mg/kg of body weight.

11. A method for treatment or control of a disease associated with cGMP phosphodiesterase activity which comprises administering to a patient a cGMP phosphodiesterase inhibiting effective amount of a pharmaceutical composition comprising a compound of the formula I

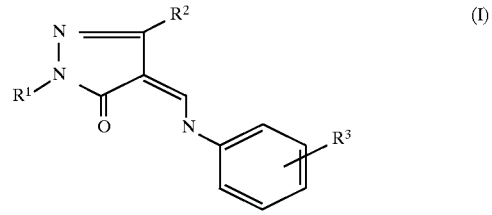

in which

R¹ is benzyl; alkoxybenzyl with 1–3 C atoms in the alkoxy moiety; phenyl; phenyl which is substituted once to three times by amino, halogen, nitro, HSO₃—, cyano, carboxyl, A—O—CO—, A—CO—NH—, A—CO—NA—, carbamoyl, N-alkylcarbamoyl, N,N-dialkylcarbamoyl with 1–6 C atoms in each alkyl moiety, A—SO₂—NH—, A—SO₂—NA—, SO₂NR⁴R⁵ (where R⁴ and R⁵ are independently H or alkyl with 1–6 C atoms or NR⁴R⁵ is a 5- or 6-membered ring, optionally with other heteroatoms N, S or O which ring is optionally substituted by A), A—CO—NH—SO₂—, A—CO—NA—SO₂—, acylsulfonamido, tetrazolyl or phospho; or pyridyl;

A is straight or branched alkyl with 1–6 C atoms or straight or branched fluorine- or chlorine substituted alkyl with 1–6 C atoms, R² is alkyl with 1–5 C atoms, alkoxycarbonylalkyl, hydroxyalkyl or hydroxycarbonylalkyl;

R³ is H, straight-chain or branched alkyl with 1–5 C atoms, straight-chain or branched alkoxy with 1–5 C atoms, fluorine- or chlorine-substituted alkyl, aminoalkanoyl, aminoalkyl, $SO_2NR^4R^5$ where $R^4$ is H or alkyl with 2–6 C atoms and $R^5$ is alkyl with 2–6 C atoms or $NR^4R^5$ is a 5- or 6-membered ring, optionally with other heteroatoms N, S or O,
or a physiologically acceptable salt thereof and
a solid, liquid or semi-liquid vehicle or auxiliary.

12. The method of claim 11, wherein the disease is treated or controlled by selective inhibition of cGMP-specific phosphodiesterase.

13. The method of claim 11, wherein the disease is a disorder of the cardiovascular system, heart failure or both.

* * * * *